(12) United States Patent
Randall et al.

(10) Patent No.: US 11,279,901 B2
(45) Date of Patent: *Mar. 22, 2022

(54) TREATMENT COMPOSITIONS COMPRISING LOW LEVELS OF AN OLIGOAMINE

(71) Applicant: The Procter & Gamble Company, Cincinnati, OH (US)

(72) Inventors: Sherri Lynn Randall, Hamilton, OH (US); Fabrizio Meli, Montgomery, OH (US); Gregory Scot Miracle, Liberty Township, OH (US); Patrick Christopher Stenger, Fairfield, OH (US); Kerry Andrew Vetter, Cincinnati, OH (US); Giulia Ottavia Bianchetti, Brussels (BE)

(73) Assignee: The Procter & Gamble Company, Cincinnati, OH (US)

( * ) Notice: Subject to any disclaimer, the term of this patent is extended or adjusted under 35 U.S.C. 154(b) by 66 days.

This patent is subject to a terminal disclaimer.

(21) Appl. No.: 16/547,621

(22) Filed: Aug. 22, 2019

(65) Prior Publication Data
US 2020/0063068 A1 Feb. 27, 2020

(30) Foreign Application Priority Data

Aug. 24, 2018 (EP) .................... 18190606

(51) Int. Cl.
| | |
|---|---|
| C11D 3/30 | (2006.01) |
| C07C 211/14 | (2006.01) |
| C11D 3/42 | (2006.01) |
| C11D 1/83 | (2006.01) |
| C11D 3/386 | (2006.01) |
| C11D 1/14 | (2006.01) |
| C11D 1/75 | (2006.01) |
| C11D 1/24 | (2006.01) |

(52) U.S. Cl.
CPC ............. C11D 3/30 (2013.01); C07C 211/14 (2013.01); C11D 1/83 (2013.01); C11D 3/38618 (2013.01); C11D 3/42 (2013.01); C11D 1/146 (2013.01); C11D 1/24 (2013.01); C11D 1/75 (2013.01)

(58) Field of Classification Search
CPC .... C11D 1/14; C11D 3/30; C11D 3/33; C11D 3/86; C11D 3/38618
USPC ................ 510/280, 300, 306, 321, 499, 503
See application file for complete search history.

(56) References Cited

U.S. PATENT DOCUMENTS

| | | |
|---|---|---|
| 3,003,970 A | 10/1961 | Call |
| 3,776,850 A | 12/1973 | Pearson et al. |
| 4,192,692 A | 3/1980 | Herrmann |
| 4,556,509 A | 12/1985 | Demangeon |
| 5,728,668 A | 3/1998 | Thomas |
| 6,369,024 B1 | 4/2002 | Panandiker |
| 6,525,013 B1 | 2/2003 | Littig et al. |
| 6,680,289 B1 | 1/2004 | Woo |
| 6,710,023 B1 | 3/2004 | Bodet |
| 6,750,189 B1 | 6/2004 | Zhang |
| 6,951,710 B2 | 10/2005 | Rieker |
| 7,018,968 B2 | 3/2006 | Hsu |
| 7,083,801 B2 | 8/2006 | El A Nma |
| 7,387,992 B2 | 6/2008 | Hsu |
| 7,517,847 B2 | 4/2009 | Catalfamo |
| 8,193,144 B2 | 6/2012 | Tanner |
| 9,677,032 B2 | 6/2017 | Hulskotter |
| 9,752,101 B2 | 9/2017 | Loughnane |
| 9,821,081 B2 | 11/2017 | Williams |
| 2004/0038852 A1 | 2/2004 | Brown |
| 2005/0130859 A1 | 6/2005 | Gupta et al. |
| 2006/0287219 A1 | 12/2006 | Dykstra |
| 2010/0305020 A1 | 12/2010 | Jennewein |
| 2011/0183883 A1 | 7/2011 | Hahn |
| 2011/0188784 A1 | 8/2011 | Denome |
| 2014/0147408 A1 | 5/2014 | Williams |
| 2014/0201927 A1 | 7/2014 | Bianchetti et al. |
| 2014/0323383 A1 | 10/2014 | Trujillo |
| 2015/0217015 A1 | 8/2015 | Williams |
| 2015/0267155 A1 | 9/2015 | Brooker et al. |
| 2015/0275142 A1 | 10/2015 | Hulskotter |
| 2015/0275144 A1 | 10/2015 | Hulskotter et al. |
| 2015/0315525 A1* | 11/2015 | Hulskotter ............... C11D 1/94 510/235 |
| 2015/0353869 A1 | 12/2015 | Stenger et al. |
| 2016/0068785 A1 | 3/2016 | Vinson et al. |
| 2016/0090562 A1 | 3/2016 | Loughnane et al. |
| 2016/0340625 A1 | 11/2016 | Scheibel et al. |
| 2017/0067003 A1 | 3/2017 | Souter et al. |
| 2017/0137745 A1 | 5/2017 | Tang |
| 2017/0191004 A1 | 7/2017 | Schmaelzle |
| 2017/0253836 A1* | 9/2017 | Scheibel ............. C11D 11/0017 |

(Continued)

FOREIGN PATENT DOCUMENTS

| | | |
|---|---|---|
| CN | 1197479 A | 10/1998 |
| CN | 1224449 A | 7/1999 |

(Continued)

OTHER PUBLICATIONS

"Ethyleneamines", DOW Publication, pp. 1-16, www.dow.com.
15334F EP Search Report for appl. No. 18190606.6-1105, dated Mar. 19, 2019, 10 pages.
15335F EP Search Report for appl. No 18190607.4-1105, dated Mar. 19, 2019, 11 pages.
15334 PCT Search Report for appl. No. PCT/US2019/046479, dated Nov. 4, 2019, 16 pgs.

(Continued)

*Primary Examiner* — Gregory R Delcotto
(74) *Attorney, Agent, or Firm* — Gregory S. Darley-Emerson

(57) ABSTRACT

Treatment compositions that include relatively low levels of an oligoamine. Related methods of use and preparation.

14 Claims, No Drawings

(56) References Cited

U.S. PATENT DOCUMENTS

| | | |
|---|---|---|
| 2017/0253838 A1* | 9/2017 | Scheibel ............. C11D 11/0017 |
| 2017/0275565 A1* | 9/2017 | Scialla .................. G06F 30/392 |
| 2017/0306267 A1 | 10/2017 | Haetzelt et al. |
| 2018/0000705 A1 | 1/2018 | Marsh |
| 2018/0000706 A1 | 1/2018 | Marsh |
| 2018/0216053 A1 | 8/2018 | Denome |
| 2019/0010426 A1 | 1/2019 | Scialla |
| 2020/0063066 A1 | 2/2020 | Depoot et al. |
| 2020/0063067 A1 | 2/2020 | Depoot et al. |
| 2020/0063069 A1 | 2/2020 | Randall et al. |

FOREIGN PATENT DOCUMENTS

| | | |
|---|---|---|
| CN | 105492586 A | 4/2016 |
| EP | 3138899 A1 | 3/2017 |
| JP | 5875766 B2 | 1/2011 |
| WO | WO0049125 A1 | 8/2000 |
| WO | WO2005026302 A1 | 3/2005 |
| WO | 2009148801 A1 | 12/2009 |
| WO | WO2016106362 A1 | 6/2016 |

OTHER PUBLICATIONS

All Office Actions, U.S. Appl. No. 16/547,625.
All Office Actions; U.S. Appl. No. 16/543,660.
All Office Actions; U.S. Appl. No. 16/543,670.

* cited by examiner

TREATMENT COMPOSITIONS COMPRISING LOW LEVELS OF AN OLIGOAMINE

FIELD OF THE INVENTION

The present disclosure relates to treatment compositions comprising low levels of certain oligoamines. The present disclosure further relates to related methods of use and preparation of such compositions.

BACKGROUND OF THE INVENTION

Many treatment processes, such as laundry wash processes, are designed to eliminate soils from surfaces, such as fabrics. Some soils can cause malodors on fabrics, which may persist or even form after the treatment process is finished. Thus, manufacturers of consumer products and industrial cleaning products are continuously seeking to provide compositions and processes that provide improved malodor control.

Separately, certain polyamines or oligoamines are known to be used in detergent compositions. Such polyamines or oligoamines may facilitate certain cleaning benefits, such as grease removal. However, at the levels typically required to provide such benefits, the polyamines may cause discoloration, such as yellowing, on the target surface, such as a fabric, for example due to reactivity of the polyamines or oligoamines with various species on or around the fabric surface.

There is a need for improved treatment compositions that provide malodor benefits, preferably without significant discoloration/yellowing problems.

SUMMARY OF THE INVENTION

The present disclosure relates to treatment compositions that include certain oligoamines at relatively low levels.

For example, the present disclosure relates to a treatment composition including: from about 0.01% to about 1.0%, by weight of the treatment composition, of an oligoamine and/or a salt thereof, where the oligoamine has a structure according to according to Formula I:

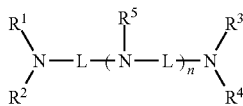

Formula I

Where each L is independently —$(C_mH_{2m})$—, where the index m is independently for each L an integer from 2 to 6, n is an integer from 1 to 10, and each of $R^1$-$R^5$ is independently selected from H and $C_1$-$C_4$ alkyl, preferably where at least one of $R^1$-$R^5$ is H; and an additional treatment adjunct.

The present disclosure also relates to a process of treating a surface, the process including the steps of: providing a surface, preferably a fabric, more preferably a fabric soiled with sebum, and contacting the surface with a composition according to the present disclosure, optionally in the presence of water.

DETAILED DESCRIPTION OF THE INVENTION

The present disclosure relates to treatment compositions that include low levels of an oligoamine of a certain structure. It has been found that such oligoamines can provide surprising malodor benefits, for example with regard to laundered fabrics.

Without wishing to be bound by theory, it is believed that metal ions, such as copper ions (e.g., $Cu^{2+}$), in a treatment liquor can facilitate the breakdown of certain soils, such as sebum, on a target surface. Such breakdown may release volatile, malodorous compounds into the air. It is believed that the oligoamines of the present disclosure can chelate and sequester copper ions in a treatment liquor, and thereby inhibit the release of such malodorous compounds.

Furthermore, it has been found that the oligoamines of the present disclosure are effective at surprisingly low levels. The low oligoamine levels are efficient with regard to cost and formulation space. Additionally, due to the low levels of oligoamine, the treated surfaces show little to no discoloration or yellowing. As described above, oligoamines are known to provide certain cleaning benefits, but generally they must be formulated at higher levels to see such benefits. Thus, the manufacturer would have little reason to expect a meaningful benefit at such low levels of oligoamines according to the present disclosure.

The compositions and processes of the present disclosure are described in more detail below.

As used herein, the articles "a" and "an" when used in a claim, are understood to mean one or more of what is claimed or described. As used herein, the terms "include," "includes," and "including" are meant to be non-limiting. The compositions of the present disclosure can comprise, consist essentially of, or consist of, the components of the present disclosure.

The terms "substantially free of" or "substantially free from" may be used herein. This means that the indicated material is at the very minimum not deliberately added to the composition to form part of it, or, preferably, is not present at analytically detectable levels. It is meant to include compositions whereby the indicated material is present only as an impurity in one of the other materials deliberately included. The indicated material may be present, if at all, at a level of less than 1%, or less than 0.1%, or less than 0.01%, or even 0%, by weight of the composition.

As used herein the phrase "fabric care composition" includes compositions and formulations designed for treating fabric. Such compositions include but are not limited to, laundry cleaning compositions and detergents, fabric softening compositions, fabric enhancing compositions, fabric freshening compositions, laundry prewash, laundry pretreat, laundry additives, spray products, dry cleaning agent or composition, laundry rinse additive, wash additive, post-rinse fabric treatment, ironing aid, unit dose formulation, delayed delivery formulation, detergent contained on or in a porous substrate or nonwoven sheet, dryer sheet, and other suitable forms that may be apparent to one skilled in the art in view of the teachings herein. Such compositions may be used as a pre-laundering treatment, a post-laundering treatment, or may be added during the rinse or wash cycle of the laundering operation.

As used herein, "liquid" includes free-flowing liquids, as well as pastes, gels, foams and mousses. Non-limiting examples of liquids include light duty and heavy duty liquid detergent compositions, fabric enhancers, detergent gels commonly used for laundry, bleach and laundry additives. Gases, e.g., suspended bubbles, or solids, e.g. particles, may be included within the liquids. Liquid compositions may have from about 0% to about 90%, or from about 30% to about 90%, or from about 50% to about 80%, by weight of the composition, of water, and may include non-aqueous liquid detergents.

A "solid" as used herein includes, but is not limited to, powders, agglomerates, and mixtures thereof. Non-limiting examples of solids include: granules, micro-capsules, beads, flakes, noodles, and pearlised balls.

Unless otherwise noted, all component or composition levels are in reference to the active portion of that component or composition, and are exclusive of impurities, for example, residual solvents or by-products, which may be present in commercially available sources of such components or compositions.

All temperatures herein are in degrees Celsius (° C.) unless otherwise indicated. Unless otherwise specified, all measurements herein are conducted at 20° C. and under the atmospheric pressure.

In all embodiments of the present disclosure, all percentages are by weight of the total composition, unless specifically stated otherwise. All ratios are weight ratios, unless specifically stated otherwise.

It should be understood that every maximum numerical limitation given throughout this specification includes every lower numerical limitation, as if such lower numerical limitations were expressly written herein. Every minimum numerical limitation given throughout this specification will include every higher numerical limitation, as if such higher numerical limitations were expressly written herein. Every numerical range given throughout this specification will include every narrower numerical range that falls within such broader numerical range, as if such narrower numerical ranges were all expressly written herein.

Treatment Composition

The present disclosure relates to treatment compositions that are suitable for treating a surface. The treatment compositions may contain an oligoamine, typically at a relatively low level, and additional treatment adjuncts. The treatment composition may be a fabric care composition, such as a laundry detergent composition.

The compositions of the present disclosure may be fabric care compositions. Such compositions may be used as a pre-laundering treatment, a post-laundering treatment, or may be added during the rinse or wash cycle of the laundering operation. It may also be used in a dry cleaning context.

The composition may be selected from the group of light duty liquid detergents compositions, heavy duty liquid detergent compositions, detergent gels commonly used for laundry, bleaching compositions, laundry additives, fabric enhancer compositions, and mixtures thereof. The composition may be a heavy duty liquid detergent composition or a fabric enhancer composition. The composition may be intended to be used during a wash cycle and/or during a rinse cycle of an automatic washing machine.

The treatment composition may be a hard surface cleaning, suitable for treating hard surfaces such as tile, porcelain, countertops, and the like.

The composition may be in any suitable form. The composition may be in the form of a liquid composition, a granular composition, a single-compartment pouch, a multi-compartment pouch, a dissolvable sheet, a pastille or bead, a fibrous article, a tablet, a bar, a flake, a dryer sheet, or a mixture thereof. The composition can be selected from a liquid, solid, or combination thereof.

The cleaning composition may be in the form of a unitized dose article, such as a tablet, a pouch, a sheet, or a fibrous article. Such pouches typically include a water-soluble film, such as a polyvinyl alcohol water-soluble film, that at least partially encapsulates a composition. Suitable films are available from MonoSol, LLC (Indiana, USA). The composition can be encapsulated in a single or multi-compartment pouch. A multi-compartment pouch may have at least two, at least three, or at least four compartments. A multi-compartmented pouch may include compartments that are side-by-side and/or superposed. The composition contained in the pouch or compartments thereof may be liquid, solid (such as powders), or combinations thereof. Pouched compositions may have relatively low amounts of water, for example less than about 20%, or less than about 15%, or less than about 12%, or less than about 10%, or less than about 8%, by weight of the detergent composition, of water.

The oligoamine and additional treatment adjuncts of the present disclosure are described in more detail below.

Oligoamine

The treatment compositions of the present disclosure include an oligoamine or a salt thereof. Oligoamines according to the present disclosure comprise amine functions, which can be primary, secondary, or tertiary amines, connected through specific alkylene groups. Without wishing to be bound by theory, it is believed that oligoamines of the present disclosure are well-suited for chelating certain metals, such as copper ($Cu^{2+}$), and that such chelation may provide malodor control benefits.

The treatment compositions according to the present disclosure may comprise relatively low levels of an oligoamine. As described above, it has surprisingly been found that low levels of the present oligoamines may provide malodour-control benefits with minimal discoloration/yellowing negatives. The treatment compositions of the present disclosure may comprise from about 0.01% to about 1.0%, or to about 0.75%, or to about 0.5%, or to about 0.4%, or to about 0.3%, or to about 0.2%, or to about 0.15%, by weight of the treatment composition, of the oligoamine. For the purposes of the present disclosure, the weight percent of the linear oligoamine is calculated using the weight of the free base form.

The oligoamines of the present disclosure may be considered linear oligoamines By "linear," it is meant that there are no further amine-containing side chains grafted on the oligoamine backbone represented by Formula I. However, it is understood that the linear oligoamine may, at least in some cases, have alkyl groups that are attached to oligoamine backbone, such as methyl or ethyl groups.

The oligoamines of the present disclosure may have a structure according to Formula I:

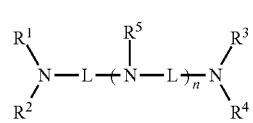

Formula I wherein each L is independently —$(C_mH_{2m})$—, wherein the index m is independently for each L an integer from 2 to 6, preferably m is 2 or 3, more preferably m is 2 (e.g., ethylene groups);

n is an integer from 1 to 10, preferably from 1 to 5 (i.e. triamines, tetramines, pentamines, hexamines, heptamines, etc.), more preferably from 1 to 3, even more preferably from 1 to 2, most preferably 1; and wherein each of $R^1$-$R^5$ is independently selected from H and $C_1$-$C_4$ alkyl, preferably H and methyl (i.e., $C_1$ alkyl). It is understood that when n is greater than 1, each $R^5$ is independently selected from the provided group, although each $R^5$ may be identical.

The index m may be independently for each L an integer from 2 to 6, wherein the index m is 2 or 3, preferably 2, for each of two L groups that are directly connected to a common N atom. It is believed that having two such L groups adjacent to a common N atom will facilitate improved metal sequestration, even if other L groups are relatively larger (e.g., have m being greater than 2).

Each of $R^1$-$R^5$ may be H. $R^5$ may be methyl. $R^5$ may be H. One or both of $R^1$ and $R^3$ may be methyl. $R^1$ and $R^3$ may be methyl, and $R^2$ and $R^4$ may both be hydrogen. Each of $R^1$-$R^5$ may be methyl. It may be preferred that at least one of $R^1$-$R^5$ is H, and even more preferred that at least one of $R^1$-$R^4$ is H. $R^1$-$R^4$ may be H, and $R^5$ may be independently selected from H and $C_1$ alkyl.

The present compositions may include an oligoamine having a structure according to Formula I above, wherein L, m, n, and $R^1$-$R^5$ are defined as above, with the proviso that if n is equal to 1, then $R^5$ is selected from H and a moiety having from 1 to 10 carbons, or from 1 to 6 carbons, or from 1 to 4 carbons.

Depending on the product type and/or overall benefit space desired, the formulator may select oligoamines having primary, secondary, and/or tertiary nitrogens, particularly at the terminal positions. Without wishing to be bound by theory, it is believed the presence of primary nitrogens in the present oligoamines may provide improved malodor control benefits, believed to be due to improved chelation efficiency and/or coordination to a target surface, such as a fabric. Also without wishing to be bound by theory, it is believed that tertiary nitrogens in the present oligoamines may result in fewer interactions with other materials in the treatment composition, for example reactions with certain perfume materials that may otherwise result in reactions (e.g., Schiff base reactions) and consequent color changes in liquid products.

Treatment compositions comprising mixtures of various oligoamines according to Formula I are also part of the scope of the present disclosure.

Suitable oligoamines according to the present disclosure may include diethylenetriamine (DETA), 4-methyl diethylenetriamine (4-MeDETA), dipropylenetriamine (DPTA), 5-methyl dipropylenetriamine (5-MeDPTA), triethylenetetraamine (TETA), 4-methyl triethylenetetraamine (4-MeTETA), 4,7-dimethyl triethylenetetraamine (4,7-Me$_2$TETA), 1,1,4,7,7-pentamethyl diethylenetriamine (M5-DETA), tripropylenetetraamine (TPTA), tetraethylenepentaamine (TEPA), tetrapropylenepentaamine (TPPA), pentaethylenehexaamine (PEHA), pentapropylenehexaamine (PPHA), hexaethyleneheptaamine (HEHA), hexapropyleneheptaamine (HPHA), N,N'-Bis(3-aminopropyl)ethylenediamine, or mixtures thereof.

The oligoamine may preferably be selected from diethylenetriamine (DETA), 4-methyl diethylenetriamine (4-MeDETA), 1,1,4,7,7-pentamethyl diethylenetriamine (M5-DETA), dipropylenetriamine (DPTA), 5-methyl dipropylenetriamine (5-MeDPTA), triethylenetetramine (TETA), tripropylenetetraamine (TPTA), tetraethylenepentaamine (TEPA), tetrapropylenepentaamine (TPTA), N,N'-Bis(3-aminopropyl)ethylenediamine, and mixtures thereof, more preferably diethylenetriamine (DETA), 4-methyl diethylenetriamine (4-MeDETA), 1,1,4,7,7-pentamethyl diethylenetriamine (M5-DETA), triethylenetetramine (TETA), tetraethylenepentaamine (TEPA), N,N'-Bis(3-aminopropyl)ethylenediamine, and mixtures thereof, even more preferably diethylenetriamine (DETA), 4-methyl diethylenetriamine (4-MeDETA), N,N'-Bis(3-aminopropyl)ethylenediamine, and mixtures thereof, most preferably diethylenetriamine (DETA). DETA may be preferred due to its low molecular weight and/or relatively low cost to produce.

The oligoamine may comprise diethylene triamine ("DETA," where m is equal to 2, n is equal to 1, and each of $R^1$-$R^5$ is H), or a derivative thereof, including alkylated forms (e.g., where one or more of $R^1$-$R^5$ is an alkyl group, such as methyl). The oligoamine may comprise at least 80% or even at least 90% or even at least 95% by weight of the oligoamine of a form of diethylene triamine (DETA), even more preferably the oligoamine consists of a form of diethylene triamine (DETA). The oligoamine may be selected from: DETA; 4-methyl DETA; and mixtures thereof; preferably DETA (unalkylated diethylene triamine).

Depending on the finished product or wash solution pH, the nitrogen atoms may be protonated, partially or fully, resulting in the salt form of the oligoamine according to Formula I. These (partially) protonated oligoamines are also considered as part of the scope of the present disclosure. It may be that when the oligoamine is in salt form, the salt is not a salt of an anionic surfactant.

The oligoamines of the present disclosure may have a molecular weight of between about 100 to about 1200 Da, or from about 100 to about 900 Da, or from about 100 to about 600 Da, or from about 100 to about 400 Da, preferably between about 100 Da and about 250 Da, most preferably between about 100 Da and about 175 Da, or even between about 100 Da and about 150 Da. For purposes of the present disclosure, the molecular weight is determined using the free base form of the oligoamine.

A skilled person in the art will know how to obtain oligoamines according to the present disclosure. For example, oligoamines according to Formula I where L has m equal to 2 may be obtained by reactions involving ammonia and ethylene dichloride, followed by fractional distillation. The common oligoamines obtained are diethylenetriamine (DETA), triethylenetetramine (TETA), and tetraethylenepentamine (TEPA). Other oligoamines according to Formula I may be formed, where m is equal to from 2 to 6 via use of the appropriate halogen-disubstituted alkylenes.

Above the pentamines, i.e the hexamines, heptamines, octamines, and possibly nonamines, the cogenerically derived mixture does not appear to separate by distillation and can include other materials such as cyclic amines and particularly piperazines.

Suitable ethylene-based oligoamines according to the present disclosure are commercially available from multiple chemical suppliers including Dow, BASF, Huntsman, and Akzo Nobel Corporations.

Additional Treatment Adjunct

The treatment compositions of the present disclosure may include an additional treatment adjunct. The additional treatment adjuncts may be suitable for delivering a treatment benefit to a target surface, such as a fabric or other textile. Treatment adjuncts, as used herein, may also include agents that facilitate chemical or physical stability in the treatment compositions, such as buffers, structurants/thickeners, and/or carriers.

The treatment adjunct(s) may be present in the composition at levels suitable for the intended use of the composition. Typical usage levels range from as low as 0.001% by weight of composition for adjuncts such as optical brighteners to 50% by weight of composition for surfactants.

The treatment adjunct may include a surfactant system, antioxidant, hueing agent, optical brightener, additional chelating agents, enzymes, fatty acids and/or salts thereof, encapsulated benefit agents, soil release polymers, builders, dye transfer inhibiting agents, dispersants, enzyme stabilizers, catalytic materials, bleaching agents, bleach catalysts, bleach activators, polymeric dispersing agents, soil removal/anti-redeposition agents, polymeric grease cleaning agents, amphiphilic copolymers, suds suppressors, aesthetic dyes, perfume (including encapsulated perfume), structure elasticizing agents, fabric softeners, carriers, fillers, hydrotropes, solvents, anti-microbial agents and/or preservatives, neutralizers and/or pH adjusting agents, processing aids, fillers, rheology modifiers or structurants, opacifiers, pearlescent agents, pigments, anti-corrosion and/or anti-tarnishing agents, antifoams, chlorine scavengers, and mixtures thereof.

The treatment adjunct may include a surfactant system, an antioxidant, a whitening or brightening agents such as a hueing agent or an optical brightener, an additional chelant, an enzyme, or mixtures thereof. The additional adjunct may include an encapsulated benefit agent, which may be encapsulated perfume, preferably where the encapsulated perfume comprises a shell surrounding a core, preferably where the shell comprises amine compounds and/or acrylate polymers.

Several treatment adjuncts are discussed in more detail below.

Surfactant System

Compositions according to the present disclosure may include a surfactant system. The surfactant system may consist of one type of surfactant. The surfactant system may include more than one surfactant. In particular, laundry detergents (such as heavy duty liquid laundry detergents) may include surfactant systems, including systems that include anionic surfactant.

The compositions of the present disclosure may include from about from about 1% to about 90%, or from about 1% to about 80%, or from about 1% to about 70%, or from about 2% to about 60%, or from about 5% to about 50%, by weight of the composition, of a surfactant system. Liquid compositions may include from about 5% to about 40%, by weight of the composition, of a surfactant system. Compact formulations, including compact liquids, gels, and/or compositions suitable for a unit dose form, may include from about 25% to about 90%, or from about 25% to about 70%, or from about 30% to about 50%, by weight of the composition, of a surfactant system.

The surfactant system may include anionic surfactant, nonionic surfactant, zwitterionic surfactant, cationic surfactant, amphoteric surfactant, or combinations thereof. The surfactant system may include linear alkyl benzene sulfonate, alkyl ethoxylated sulfate, alkyl sulfate, alkyl ethoxylated carboxylates, nonionic surfactant such as ethoxylated alcohol, amine oxide, or mixtures thereof. The surfactants may be, at least in part, derived from natural sources, such as natural feedstock alcohols.

The surfactant system may include anionic surfactant. The mole ratio of anionic surfactant to protonatable amines in the oligoamine may be less than about 15:1. In such cases, the oligoamine may have a structure according to Formula I, wherein index n is an integer from 2 to 5.

Suitable anionic surfactants may include any conventional anionic surfactant. This may include a sulfate detersive surfactant, for e.g., alkoxylated and/or non-alkoxylated alkyl sulfate materials, and/or sulfonic detersive surfactants, e.g., alkyl benzene sulfonates. The anionic surfactants may be linear, branched, or combinations thereof. Preferred surfactants include linear alkyl benzene sulfonate (LAS), alkyl ethoxylated sulfate (AES), alkyl sulfates (AS), or mixtures thereof. Other suitable anionic surfactants include branched modified alkyl benzene sulfonates (MLAS), methyl ester sulfonates (MES), and/or alkyl ethoxylated carboxylates (AEC). The anionic surfactants may be present in acid form, salt form, or mixtures thereof. The anionic surfactants may be neutralized, in part or in whole, for example, by an alkali metal (e.g., sodium) or an amine (e.g., monoethanolamine). The anionic surfactant may be pre-neutralized, preferably with an alkali metal, an alkali earth metal, an amine such as an ethanolamine, or mixtures thereof. It is preferred that the anionic surfactant is not (pre-)neutralized with the oligoamine of the present disclosure.

The surfactant system may include nonionic surfactant. Suitable nonionic surfactants include alkoxylated fatty alcohols, such as ethoxylated fatty alcohols. Other suitable nonionic surfactants include alkoxylated alkyl phenols, alkyl phenol condensates, mid-chain branched alcohols, mid-chain branched alkyl alkoxylates, alkylpolysaccharides (e.g., alkylpolyglycosides), polyhydroxy fatty acid amides, ether capped poly(oxyalkylated) alcohol surfactants, and mixtures thereof. The alkoxylate units may be ethyleneoxy units, propyleneoxy units, or mixtures thereof. The nonionic surfactants may be linear, branched (e.g., mid-chain branched), or a combination thereof. Specific nonionic surfactants may include alcohols having an average of from about 12 to about 16 carbons, and an average of from about 3 to about 9 ethoxy groups, such as C12-C14 EO7 nonionic surfactant.

Suitable zwitterionic surfactants may include any conventional zwitterionic surfactant, such as betaines, including alkyl dimethyl betaine and cocodimethyl amidopropyl betaine, $C_8$ to $C_{18}$ (for example from $C_{12}$ to $C_{18}$) amine oxides (e.g., $C_{12-14}$ dimethyl amine oxide), and/or sulfo and hydroxy betaines, such as N-alkyl-N,N-dimethylammino-1-propane sulfonate where the alkyl group can be $C_8$ to $C_{18}$, or from $C_{10}$ to $C_{14}$. The zwitterionic surfactant may include amine oxide.

Fabric Conditioning Active

The treatment compositions of the present disclosure may include a fabric conditioning active (FCA). Compositions comprising such actives, such as liquid fabric enhancing compositions, may be useful for providing various benefits to target fabrics, including softness, anti-wrinkle, anti-static, conditioning, anti-stretch, color and/or appearance benefits. Fabric conditioning actives (FCAs) suitable for compositions of the present disclosure may include quaternary ammonium ester compounds, silicones, non-ester quaternary ammonium compounds, amines, fatty esters, sucrose esters, silicones, dispersible polyolefins, polysaccharides, fatty acids, softening or conditioning oils, polymer latexes, or combinations thereof.

Antioxidant

The compositions of the present disclosure may include an antioxidant. Without wishing to be bound by theory, it is believed that antioxidants may help to improve malodor control and/or cleaning performance of the compositions, particularly in combination with the oligoamines of the present disclosure. Antioxidants may also help to reduce yellowing that may be associated with amines, allowing the amines to be formulated at a relatively higher level. Antioxidants are substances as described in Kirk-Othmer (Vol. 3, page 424) and in Ullmann's Encyclopedia (Vol. 3, page 91).

The compositions of the present disclosure may include an antioxidant, preferably a hindered phenol antioxidant, in an amount of from about 0.001% to about 2%, preferably from about 0.01% to about 0.5%, by weight of the composition.

Suitable antioxidants may include alkylated phenols, having the general formula:

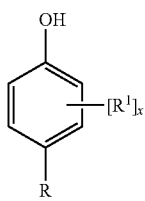

wherein R is $C_1$-$C_{22}$ linear alkyl or $C_3$-$C_{22}$ branched alkyl, each (1) having optionally therein one or more ester (—$CO_2$—) or ether (—O—) links, and (2) optionally substituted by an organic group comprising an alkyleneoxy or polyalkyleneoxy group selected from EO (ethoxy), PO (propoxy), BO (butoxy), and mixtures thereof, more preferably from EO alone or from EO/PO mixtures; R may preferably be methyl, branched $C_3$-$C_6$ alkyl, or $C_1$-$C_6$ alkoxy, preferably methoxy; $R^1$ is a $C_3$-$C_6$ branched alkyl, preferably tert-butyl; x is 1 or 2.

Preferred types of alkylated phenols having this formula may include hindered phenolic compounds. As used herein, the term "hindered phenol" is used to refer to a compound comprising a phenol group with either (a) at least one $C_3$ or higher branched alkyl, preferably a $C_3$-$C_6$ branched alkyl, preferably tert-butyl, attached at a position ortho to at least one phenolic —OH group, or (b) substituents independently selected from the group consisting of a $C_1$-$C_6$ alkoxy, preferably methoxy, a $C_1$-$C_{22}$ linear alkyl or $C_3$-$C_{22}$ branched alkyl, preferably methyl or branched $C_3$-$C_6$ alkyl, or mixtures thereof, at each position ortho to at least one phenolic —OH group. If a phenyl ring comprises more than one —OH group, the compound is a hindered phenol provided at least one such —OH group is substituted as described immediately above. Where any R group in the structure above comprises three or more contiguous monomers, that antioxidant is defined herein as a "polymeric hindered phenol antioxidant." Compositions according to the present disclosure may include a hindered phenol antioxidant. A preferred hindered phenol antioxidant includes 3,5-di-tert-butyl-4-hydroxytoluene (BHT).

A further class of hindered phenol antioxidants that may be suitable for use in the composition is a benzofuran or benzopyran derivative having the formula:

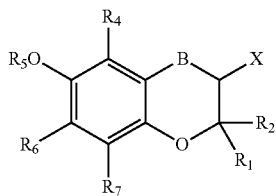

wherein $R_1$ and $R_2$ are each independently alkyl or $R_1$ and $R_2$ can be taken together to form a $C_5$-$C_6$ cyclic hydrocarbyl moiety; B is absent or $CH_2$; $R^4$ is $C_1$-$C_6$ alkyl; $R_5$ is hydrogen or —$C(O)R^3$ wherein $R_3$ is hydrogen or $C_1$-$C_{19}$ alkyl; $R_6$ is $C_1$-$C_6$ alkyl; $R_7$ is hydrogen or $C_1$-$C_6$ alkyl; X is —$CH_2OH$, or —$CH_2A$ wherein A is a nitrogen-comprising unit, phenyl, or substituted phenyl. Preferred nitrogen-comprising A units include amino, pyrrolidino, piperidino, morpholino, piperazino, and mixtures thereof.

Suitable hindered phenol antioxidants may include: 2,6-bis(1,1-dimethylethyl)-4-methyl-phenol; 3,5-bis(1,1-dimethylethyl)-4-hydroxy-benzenepropanoic acid, methyl ester; 3,5-bis(1,1-dimethylethyl)-4-hydroxybenzenepropanoic acid, octadecyl ester; or mixtures thereof.

Commercially available antioxidants that may be suitable include BHT, RALOX 35™, and/or TINOGARD TS™.

Additional antioxidants may be employed. Examples of suitable antioxidants for use in the composition include, but are not limited to, the group consisting of α-, β-, γ-, δ-tocopherol, ethoxyquin, 2,2,4-trimethyl-1,2-dihydroquinoline, 2,6-di-tert-butyl hydroquinone, tert-butyl hydroxyanisole, lignosulphonic acid and salts thereof, and mixtures thereof. It is noted that ethoxyquin (1,2-dihydro-6-ethoxy-2,2,4-trimethylquinoline) is marketed under the name Raluquin™ by the company Raschig™. Other types of antioxidants that may be used in the composition are 6-hydroxy-2,5,7,8-tetramethylchroman-2-carboxylic acid (Trolox™) and 1,2-benzisothiazoline-3-one (Proxel GXL™). Antioxidants such as tocopherol sorbate, butylated hydroxyl benzoic acids and their salts, gallic acid and its alkyl esters, uric acid and its salts, sorbic acid and its salts, and dihydroxyfumaric acid and its salts may also be useful. Other useful antioxidants may include tannins, such as tannins selected from the group consisting of gallotannins, ellagitannins, complex tannins, condensed tannins, and combinations thereof.

The use of non-yellowing antioxidants, such as non-yellowing hindered phenol antioxidants, may be preferred. Antioxidants that form such yellow by-products may be avoided if they lead to perceptible negative attributes in the consumer experience (such as deposition of yellow by-products on fabric, for example). The skilled artisan is able to make informed decisions regarding the selection of antioxidants to employ.

Whitening/Brightening Agent

The additional treatment adjuncts of the present disclosure may include a whitening or brightening agent. Such agents may be selected from a hueing agent, an optical brightener, or mixtures thereof. The use of such agents may further reduce the effects of discoloration or yellowing and may enable formulation of the oligoamines at higher levels.

The compositions of the present disclosure may include a hueing agent. It has surprisingly been found that graft polymers according to the present disclosure may inhibit transfer of fugitive dyes, while having little effect on the deposition and/or performance of hueing agents on target fabrics.

Hueing agents (sometimes referred to as hueing dyes, fabric shading dyes, or bluing or whitening agents) typically provides a blue or violet shade to fabric. Such agent(s) are well known in the art and may be used either alone or in combination to create a specific shade of hueing and/or to shade different fabric types. The hueing agent may be selected from any suitable chemical class of dye as known in the art, including but not limited to acridine, anthraquinone (including polycyclic quinones), azine, azo (e.g., monoazo, disazo, trisazo, tetrakisazo, polyazo), benzodifurane, benzodifuranone, carotenoid, coumarin, cyanine, diazahemicyanine, diphenylmethane, formazan, hemicyanine, indigoids, methane, naphthalimides, naphthoquinone, nitro, nitroso, oxazine, phthalocyanine, pyrazoles, stilbene, styryl, triarylmethane, triphenylmethane, xanthenes and mixtures thereof. The hueing agent may be selected from an azo agent, a triarylmethane agent, a triphenylmethane agent, or mixtures thereof.

Suitable hueing agents include fabric shading dyes such as small molecule dyes, polymeric dyes, and dye-clay conjugates. Preferred fabric shading dyes are selected from small molecule dyes and polymeric dyes. Suitable small molecule dyes may be selected from the group consisting of dyes falling into the Colour Index (C.I., Society of Dyers and Colourists, Bradford, UK) classifications of Acid, Direct, Basic, Reactive, Solvent or Disperse dyes.

Suitable polymeric dyes include dyes selected from the group consisting of polymers containing covalently bound (sometimes referred to as conjugated) chromogens, (also known as dye-polymer conjugates), for example polymers with chromogen monomers co-polymerized into the backbone of the polymer and mixtures thereof. Preferred polymeric dyes comprise the optionally substituted alkoxylated dyes, such as alkoxylated triphenyl-methane polymeric colourants, alkoxylated carbocyclic and alkoxylated heterocyclic azo colourants including alkoxylated thiophene polymeric colourants, and mixtures thereof, such as the fabric-substantive colorants sold under the name of Liquitint® (Milliken, Spartanburg, S.C., USA).

Suitable dye clay conjugates include dye clay conjugates selected from the group comprising at least one cationic/basic dye and a smectite clay; a preferred clay may be selected from the group consisting of Montmorillonite clay, Hectorite clay, Saponite clay and mixtures thereof.

Pigments are well known in the art and may also be used as hueing agents in the fabric care compositions disclosed herein. Suitable pigments may include C.I Pigment Blues 15 to 20, especially 15 and/or 16, C.I. Pigment Blue 29, C.I. Pigment Violet 15, Monastral Blue, and mixtures thereof.

The amount of adjunct hueing agent present in a laundry care composition of the invention may be from 0.0001 to 0.05 wt % based on the total cleaning composition, preferably from 0.0001 to 0.005 wt %. Based on the wash liquor, the concentration of hueing agent may be from 1 ppb to 5 ppm, preferably from 10 ppb to 500 ppb.

The compositions of the present disclosure may include an optical brightener. Brighteners, also sometimes referred to as fluorescent whitening agents, may emit at least some visible light.

Commercial optical brighteners, which may be used herein, can be classified into subgroups, which include, but are not necessarily limited to, derivatives of stilbene, pyrazoline, coumarin, carboxylic acid, methinecyanines, dibenzothiphene-5,5-dioxide, azoles, 5- and 6-membered-ring heterocycles, and other miscellaneous agents. The brighteners may be added in particulate form or as a premix with a suitable solvent, for example nonionic surfactant, monoethanolamine, and/or propane diol.

Suitable fluorescent brighteners may include: disodium 4,4'-bis{[4-anilino-6-morpholino-s-triazin-2-yl]-amino}-2,2'-stilbenedisulfonate (Brightener 15, commercially available under the tradename Tinopal AMS-GX by BASF); disodium 4,4'-bis{[4-anilino-6-(N-2-bis-hydroxyethyl)-s-triazine-2-yl]-amino}-2,2'-stilbenedisulonate (commercially available under the tradename Tinopal UNPA-GX by BASF); disodium 4,4'-bis{[4-anilino-6-(N-2-hydroxyethyl-N-methylamino)-s-triazine-2-yl]-amino}-2,2'-stilbenedisulfonate (commercially available under the tradename Tinopal 5BM-GX by BASF); and/or disodium 4,4'-bis((4-amino-6-anilino-1,3,5-triazin-2-yl)amino)stilbene-2,2'-disulphonate (Brightener 49). The brightener may be Brightener 49, Brightener 15, Brightener 3, or mixtures thereof.

Additional Chelating Agent

The additional treatment adjuncts of the present disclosure may comprise an additional chelating agent (also known as a chelant or a chelator). The additional chelating agent may be selected so as to have an affinity for a metal ion that is different than the metal ion for which the oligoamine has an affinity. For example, DETA, an oligoamine according to the present disclosure, has a particular affinity for copper ions, whereas DTPA, a different chelating agent, has a particular affinity for calcium ions. Thus, a composition having a combination of chelating agents may provide a broad spectrum of sequestration, and thereby provide improved performance. It may be preferable to couple a copper-chelating agent, such as the oligoamines of the present disclosure, with a calcium-chelating agent, such as DTPA and/or HEDP, in order to optimize cleaning performance, for example, by improving/maximizing the chelant load in the composition's formulation while maintaining enzyme stability.

The additional chelating agent may be present at a level of from about 0.1% to about 10%, or to about 5%, or to about 2%, by weight of the composition. The oligoamine and the additional chelating agent(s) may be present in the treatment composition at a combined level of from about 0.1% to about 10%, preferably to about 5%, by weight of the treatment composition. The weight ratio of the oligoamine to the additional chelating agent may be from about 10:1 to about 1:50, or from about 1:1 to about 1:25, or from about 1:2 to about 1:20. The amount present by weight of oligoamine may be less than the amount present by weight of the additional chelating agent.

Suitable additional chelating agents may include phosphonates, aminocarboxylates, amino phosphonates, polyfunctionally-substituted aromatic chelating agents, or mixtures thereof, preferably aminocarboxylates. The additional chelating agents, as used herein, are not intended to include traditional builders, such as citric acid, although such builders may be present in compositions of the present disclosure.

Aminocarboxylates useful as chelating agents include, but are not limited to, ethylenediaminetetracetates, N-(hydroxyethyl)ethylenediaminetriacetates, nitrilotriacetates, ethylenediamine tetraproprionates, triethylenetetraaminehexacetates, diethylenetriamine-pentaacetates, and ethanoldiglycines, alkali metal, ammonium, and substituted ammonium salts thereof, and mixtures thereof. Aminophosphonates are also suitable for use as chelating agents in the compositions of the invention when low levels of total phosphorus are permitted, and include ethylenediaminetetrakis (methylenephosphonates). Polyfunctionally-substituted aromatic chelating agents may include catechols, for example sulphonated catechols.

The additional chelant may include: DTPA (diethylenetriaminepentaacetic acid), HEDP (hydroxyethanediphosphonic acid), EDDS (ethylenediamine disuccinate (EDDS), DTPMP (diethylene triamine penta (methylene phosphonic acid)), EDTMP (ethylene diamine tetra(methylene phosphonic acid)), Tiron® (1,2-diydroxybenzene-3,5-disulfonic acid), HPNO (2-pyridinol-N-oxide), MGDA (methylglycinediacetic acid), GLDA (glutamic-N,N-diacetic acid), any suitable derivative thereof, salts thereof, and mixtures thereof.

Enzymes

The treatment compositions of the present disclosure may include one or more enzymes that provide cleaning performance and/or fabric care benefits. Examples of suitable enzymes include, but are not limited to, hemicellulases, peroxidases, proteases, cellulases, xylanases, lipases, phospholipases, esterases, cutinases, pectinases, mannanases, pectate lyases, keratinases, reductases, oxidases, phenoloxidases, lipoxygenases, ligninases, pullulanases, tannases, pentosanases, malanases, β-glucanases, arabinosidases, hyaluronidase, chondroitinase, laccase, amylases, nucleases (such as deoxyribonuclease and/or ribonuclease), phosphodiesterases, or mixtures thereof. Particularly preferred may be a mixture of protease, amylase, lipase, cellulase, phosphodiesterase, and/or pectate lyase. Compositions of the present disclosure may include a oligoamine of the present disclosure, a calcium-binding chelant such as DTPA, and amylase.

Other Agents

The treatment compositions of the present disclosure may include solvent, preferably organic solvent, such as a non-aminofunctional organic solvent. Suitable organic solvents may include glycerol, ethylene glycol, 1,3 propanediol, 1,2 propanediol, tetramethylene glycol, pentamethylene glycol, hexamethylene glycol, 2,3-butane diol, 1,3 butanediol, diethylene glycol, triethylene glycol, polyethylene glycol, glycerol formal dipropylene glycol, polypropylene glycol, dipropylene glycol n-butyl ether, and mixtures thereof.

The treatment compositions of the present disclosure may include chlorine scavengers. It is believed that chlorine ions in a treatment liquor, for example from hypochlorite bleach or naturally occurring in the water source, may contribute to color fading or other discoloration. A chlorine scavenger may be incorporated at a level adequate to neutralize at least about 1 ppm, or at least about 2 ppm, or at least about 5 ppm, or at least about 10 ppm chlorine in a treatment liquor. Chlorine scavengers may include amines (other than the oligoamines described above) and/or ammonium salts. Preferred amines may include those that comprise primary and/or secondary amines, and may include alkanolamines such as monoethanolamine (MEA), diethanolamine (DEA), and/or triethanolamine (TEA).

The treatment compositions of the present disclosure may contain cleaning and/or dispersing polymers, which may provide cleaning and/or whiteness benefits. Suitable cleaning and/or dispersing polymers may include: polymeric soil release agents, which may be anionic or nonionic and/or may include a terephthalate moiety; alkoxylated polyamines, such as ethoxylated and/or propoxylated polyethyleneimines (such as PEI600 EO20 and/or PEI EO24 PO16), ethoxylated hexamethylene diamines, and sulfated versions thereof; alkoxylated polycarboxylates, including those derived from polyacrylates; amphiphilic graft co-polymers, such as those derived from a polyethylene glycol backbone and having at least one pendant moiety selected from polyvinyl acetate, polyvinyl alcohol, or mixtures thereof (such as Sokalan HP22); cellulosic polymers, such as carboxymethyl cellulose, methyl cellulose, methyl hydroxyethyl cellulose, methyl carboxymethyl cellulose, and mixtures thereof; carboxylate polymers, such as a maleate/acrylate random copolymer or polyacrylate homopolymer; or mixtures thereof. Cellulosic polymers and/or carboxylate polymers may be particularly useful in dry or powdered treatment compositions, as they may be more difficult to formulate in liquid and gel forms.

It may be desirable to limit or even eliminate certain adjuncts, particularly if a detergent sourced primarily from natural or sustainable sources is desired. The detergent compositions of the present disclosure may be free of silicone, dye, brightener, or combinations thereof. The detergent compositions of the present disclosure may comprise less than 5%, or less than 3%, or less than 1%, by weight of the composition, of amine-containing compounds, with the proviso that amine oxide surfactant (if present) is not included in the total amount of amine-containing compounds.

The compositions of the present disclosure may be substantially free of selenium compounds. The compositions of the present disclosure may be substantially free of haloproparagyl compounds.

Method of Making a Composition

The present disclosure relates to methods of making fabric care compositions comprising the oligoamines described herein. The method may include combining the components of the compositions described herein in the proportions described. For example, a oligoamine according to the present disclosure may be provided and combined with at least one additional treatment adjunct to form a treatment composition.

Liquid compositions according to the present disclosure may be made according to conventional methods, for example in a batch process or in a continuous loop process.

Solid compositions according to the present disclosure may be made according to conventional methods, for example by spray-drying process or in an agglomeration process.

The detergent compositions described herein may be encapsulated in a pouch, preferably a pouch made of water-soluble film, to form a unit dose article that may be used to treat fabrics. The pouch may include one compartment, or may have multiple compartments, which may be side-by-side and/or superposed. It may be preferred that such compositions have relatively low amounts of water, for example less than about 20%, or less than about 15%, or less than about 12%, or less than about 10%, or less than about 8%, by weight of the detergent composition, of water.

Method of Using Compositions

The present disclosure relates to methods of using the compositions described herein. The detergent compositions may be a fabric care composition and may be used to treat a surface, such as a fabric or other textile.

Methods of treating a surface may include the steps of: providing a surface, preferably a fabric, and contacting the surface with a composition according to the present disclosure, as described above. The method may include agitating the fabric in the presence of water. The method may further comprise the step of carrying out a washing or cleaning operation. Water may be added before, during, or after the contacting step to form a treatment liquor. The water and/or the treatment liquor may include copper ions ($Cu^{2+}$), for example at a level of from about 0.1 ppm to about 25 ppm.

The present disclosure also relates to a process for treating, for example by machine, a fabric, preferably soiled fabric, using a composition according to the present disclosure, comprising the steps of, placing a composition according to the present disclosure into contact with the fabric to be treated, and carrying out a treatment operation, such as a washing, cleaning, or fabric-enhancing operation. The contacting step may occur during the wash cycle or during the rinse cycle of an automatic washing machine.

Any suitable washing machine may be used, for example, a top-loading or front-loading automatic washing machine. Those skilled in the art will recognize suitable machines for the relevant treatment operation. The article of the present disclosure may be used in combination with other compositions, such as fabric additives, fabric softeners, rinse aids, and the like. Additionally, the detergent compositions of the present disclosure may be used in known hand washing methods.

The present disclosure may also be directed to a method of treating a fabric, the method comprising the steps of contacting a fabric with a detergent composition described herein, carrying out a washing step, and then contacting the fabric with a fabric softening composition. The entire method, or at least the washing step, may be carried out by hand, be machine-assisted, or occur in an automatic washing machine. The step of contacting the fabric with a fabric softening composition may occur in the presence of water, for example during a rinse cycle of an automatic washing machine.

Combinations

Specifically contemplated combinations of the disclosure are herein described in the following lettered paragraphs. These combinations are intended to be illustrative in nature and are not intended to be limiting.

A. A treatment composition comprising: from about 0.01% to about 1.0%, by weight of the treatment composition, of an oligoamine and/or a salt thereof, wherein the oligoamine has a structure according to according to Formula I:

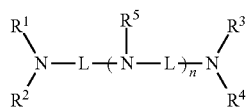

Formula I wherein each L is independently —$(C_mH_{2m})$—, wherein the index m is independently for each L an integer from 2 to 6, n is an integer from 1 to 10, and each of $R^1$-$R^5$ is independently selected from H and $C_1$-$C_4$ alkyl; and an additional treatment adjunct.

B. A treatment composition according to paragraph A, wherein the treatment composition comprises from about 0.01% to about 0.75%, or to about 0.5%, or to about 0.4%, or to about 0.3%, or to about 0.2%, or to about 0.15%, by weight of the treatment composition, of the oligoamine.

C. A treatment composition according to any of paragraphs A or B, wherein the index m is 2 or 3, preferably index m is 2.

D. A treatment composition according to any of paragraphs A-C, wherein n is an integer from 1 to 5, preferably from 1 to 3, more preferably 1 or 2, even more preferably 1.

E. A treatment composition according to any of paragraphs A-D, wherein each of $R^1$-$R^5$ is independently selected from H and $C_1$ alkyl, preferably wherein at least one of $R^1$-$R^5$ is H, more preferably wherein at least one of $R^1$-$R^4$ is H, even more preferably wherein all are H.

F. A treatment composition according to any of paragraphs A-E, wherein the oligoamine is characterized by a molecular weight of from about 100 to about 1200 Da, or from about 100 to about 900 Da, or from about 100 to about 600 Da, or from about 100 to about 400 Da, or preferably between about 100 Da and about 250 Da, more preferably between about 100 Da and about 200 Da, even more preferably between about 100 Da and about 150 Da.

G. A treatment composition according to any of paragraphs A-F, wherein the oligoamine is selected from the group consisting of: diethylenetriamine (DETA), 4-methyl diethylenetriamine (4-MeDETA), dipropylenetriamine (DPTA), 5-methyl dipropylenetriamine (5-MeDPTA), triethylenetetraamine (TETA), 4-methyl triethylenetetraamine (4-MeTETA), 4,7-dimethyl triethylenetetraamine (4,7-Me2TETA), 1,1,4,7,7-pentamethyl diethylenetriamine (M5-DETA), tripropylenetetraamine (TPTA), tetraethylenepentaamine (TEPA), tetrapropylenepentaamine (TPPA), pentaethylenehexaamine (PEHA), pentapropylenehexaamine (PPHA), hexaethyleneheptaamine (HEHA), hexapropyleneheptaamine (HPHA), N,N'-Bis(3-aminopropyl)ethylenediamine, and mixtures thereof.

H. A treatment composition according to any of paragraphs A-G, wherein the oligoamine is selected from the group consisting of diethylenetriamine (DETA), 4-methyl diethylenetriamine (4-MeDETA), 1,1,4,7,7-pentamethyl diethylenetriamine (M5-DETA), triethylenetetramine (TETA), tetraethylenepentaamine (TEPA), N,N'-Bis(3-aminopropyl)ethylenediamine, and mixtures thereof, preferably diethylenetriamine (DETA), 4-methyl diethylenetriamine (4-MeDETA), N,N'-Bis(3-aminopropyl)ethylenediamine, and mixtures thereof.

I. A treatment composition according to any of paragraphs A-H, wherein the oligoamine comprises diethylenetriamine (DETA).

J. A treatment composition according to any of paragraphs A-I, wherein the additional treatment adjunct is selected from a surfactant system, fabric conditioning active (FCA), antioxidant, hueing agent, optical brightener, additional chelating agents, enzymes, fatty acids and/or salts thereof, encapsulated benefit agents, soil release polymers, builders, dye transfer inhibiting agents, dispersants, enzyme stabilizers, catalytic materials, bleaching agents, bleach catalysts, bleach activators, polymeric dispersing agents, soil removal/anti-redeposition agents, polymeric grease cleaning agents, amphiphilic copolymers, suds suppressors, aesthetic dyes, perfume, structure elasticizing agents, fabric softeners, carriers, fillers, hydrotropes, solvents, anti-microbial agents and/or preservatives, pH adjusting agents, processing aids, fillers, rheology modifiers, structurants, opacifiers, pearlescent agents, pigments, anti-corrosion agents, anti-tarnishing agents, antifoams, chlorine scavengers, and mixtures thereof.

K. A treatment composition according to any of paragraphs A-J, wherein the additional treatment adjunct comprises a surfactant system, preferably wherein the surfactant system comprises anionic surfactant, nonionic surfactant, zwitterionic surfactant, amphoteric surfactant, cationic surfactant, or a combination thereof, more preferably wherein the surfactant system comprises anionic surfactant.

L. A treatment composition according to paragraph K, wherein the anionic surfactant is pre-neutralized, preferably with an alkali metal, an alkali earth metal, an amine, or mixtures thereof.

M. A treatment composition according to any of paragraphs K or L, wherein the mole ratio of anionic surfactant to protonatable amines in the oligoamine is less than about 15:1, preferably wherein in the oligoamine according to Formula I, index n is an integer from 2 to 5.

N. A treatment composition according to any of paragraphs A-M, wherein the additional treatment adjunct comprises an antioxidant, preferably an antioxidant comprising a hindered phenol.

O. A treatment composition according to any of paragraphs A-N, wherein the additional treatment adjunct comprises a whitening or brightening agent, preferably a whitening or brightening agent selected from a hueing agent, an optical brightener, or mixtures thereof.

P. A treatment composition according to any of paragraphs A-O, wherein the additional treatment adjunct comprises an additional chelating agent, preferably an additional chelating agent selected from phosphonates, aminocarboxylates, amino phosphonates, polyfunctionally-substituted aromatic chelating agents, or mixtures thereof, more preferably an additional chelating agent selected from DTPA (diethylenetriaminepentaacetic acid), HEDP (hydroxyethanediphosphonic acid), EDDS (ethylenediamine disuccinate (EDDS), DTPMP (diethylene triamine penta (methylene phosphonic acid)), EDTMP (ethylene diamine tetra(methylene phosphonic acid)), Tiron® (1,2-diydroxybenzene-3,5-disulfonic acid), HPNO (2-pyridinol-N-oxide), MGDA (methylglycinediacetic acid), GLDA (glutamic-N,N-diacetic acid), any suitable derivative thereof, salts thereof, and mixtures thereof.

Q. A treatment composition according to any of paragraphs A-P, wherein the weight ratio of the oligoamine to the additional chelant is from about 10:1 to about 1:50, or from about 1:1 to about 1:25, or from about 1:2 to about 1:20.

R. A treatment composition according to any of paragraphs A-Q, wherein the oligoamine and the additional chelant(s) are present in the treatment composition at a combined level of from about 0.1% to about 10%, preferably from about 0.5% to about 5%, by weight of the treatment composition.

S. A treatment composition according to any of paragraphs A-R, wherein the additional treatment adjunct comprises an enzyme, preferably wherein the enzyme is selected from protease, amylase, lipase, cellulase, phosphodiesterase, pectate lyase, and mixtures thereof.

T. A treatment composition according to any of paragraphs A-S, wherein the treatment composition is a laundry detergent composition.

U. A treatment composition according to any of paragraphs A-T, wherein the treatment composition is in the form of a liquid composition, a granular composition, a single-compartment pouch, a multi-compartment pouch, a dissolvable sheet, a pastille or bead, a fibrous article, a tablet, a bar, a flake, a dryer sheet, or a mixture thereof, preferably in the form of a liquid composition.

V. A process of treating a surface, preferably wherein the surface is a fabric, the process comprising the steps of:

providing a surface, preferably a fabric, more preferably a fabric soiled with sebum, and contacting the surface with a composition according to any of paragraphs A-U, optionally in the presence of water.

Test Methods

Malodor Reduction Test Method

The following method is used to test the malodor reduction benefits of a composition.

A. Preparation of 75 Grams Malodor Marker

Fatty acids and malodor markers are added into 100 ml glass gar with Teflon-lined cap according to Table A and mixed well using a vortex.

TABLE A

Malodor marker composition

| Material | CAS # | % Composition | Weight needed (g) |
| --- | --- | --- | --- |
| Iso Valeric acid | 503-74-2 | 12.00 | 9.0 |
| Undecanal | 112-44-7 | 0.20 | 0.15 |
| Undecanoic Acid | 112-37-8 | 62.80 | 47.1 |

TABLE A-continued

Malodor marker composition

| Material | CAS # | % Composition | Weight needed (g) |
| --- | --- | --- | --- |
| Skatole | 83-34-1 | 1.00 | 0.75 |
| Decanoic Acid | 334-48-5 | 22.00 | 16.5 |
| Ethyl undecanoate | 627-90-7 | 2.00 | 1.5 |

B. Preparation of Body Soil Malodor Composition

Provided the specified amount of each material according to Table B into a 200 mL glass jar with Teflon lined cap. Artificial body soil (ABS) is commercially available by Accurate Product Development; 2028 Bohlke Blvd, Fairfield, Ohio 45014.

TABLE B

Body soil malodor composition

| Material | Weight (g) |
| --- | --- |
| Malodor marker (from Table A) | 17.1 |
| Artificial Body Soil (ABS) | 15.8 |
| Di-propylene glycol monomethyl ether (CAS: 34590-94-8) | 105 |
| Squalene (CAS # 111-02-4) | 15.8 |

C. Preparation of Malodor Test Fabrics Sixteen malodor test fabrics per wash load are prepared by applying 300 µl of Body soil malodor composition described in Table B to de-sized 2×5 inch white polycotton 50/50 (PCW50/50) swatches. 48 grams of liquid detergent to be tested (see, e.g., Example 1, Table 1, below) is added to Duet 9200 washing appliance set to Normal cycle; 77° F. wash cycle followed by a 60° F. rinse cycle. Tap water is used, which contains an ambient level of copper, due to copper piping systems, for example. Malodor test fabrics are washed in 7 gpg wash water with 3.9 kg, 50×50 cm clean cotton and poly-cotton ballast then dried in a Maytag double stack tumble drier set to low for 20 minutes. The dried fabrics are placed in a mylar bag and sealed for 24 hours.

D. Analytical Detection of Malodor on Fabric

The malodor reduction using ABS/Squalene malodor sensors are quantitatively determined by Gas Chromatography Mass Spectroscopy using an Agilent gas chromatograph 7890B equipped with a mass selective detector (5977B), a Chemstation quantitation package and a Gerstel multi-purpose sampler equipped with a solid phase micro-extraction (SPME) probe. Calibration standards of 6-Methyl-5-hepten-2-one (CAS 110-93-0), Trans-2-heptenal (18829-55-5) and 3-methyl-2-Butenal (107-86-8) are prepared by dissolving a known weight of these materials in light mineral oil (CAS 8020-83-5) (each material available from Sigma Aldrich). Fabrics are cut into uniform 2 inch by 2.5 inch pieces and placed in 10 mL headspace crimp vials. Vials are equilibrated greater than 12 hours before analysis. The following settings are used in the auto sampler: 80 C incubation temperature, 90 min incubation time, VT32-10 sample tray type, 22 mm vial penetration, 20 min extraction time, 54 mm injection penetration and 300 s desorption time. The following settings are used for the Front Split/Splitless inlet helium: split mode, 250 C temperature, 12 psi pressure, 79.5 mL/min total flow, 3 mL/min septum purge flow, 50:1 split ratio and 22.5 min GC run time. The follow settings are used in the oven: 40 C initial temperature, 12 C/min heating program, 250 C temperature and 5 min hold time. Based on the partition coefficients (K at 80 C) of each component, the total nMol/L liter of 6-Methyl-5-hepten-2-one (K=3353), Trans-2-heptenal (K=3434), and 3-methyl-2-Butenal (K=1119) are calculated.

These values of these three measurements (in nmoles/L) are added together to provide the Total ABS/Squalene Markers (nmoles/L) for a given test leg.

E. % Malodor Reduction Oxidation Products Calculations

The % Malodor Reduction Oxidation Products is provided as a percentage comparing the reduction of the amount of selected malodor markers as provided by the test composition compared to the (nil-oligoamine) reference composition. The value is determined as follows:

% Reduction Oxidation Products=(Markers$_{ref}$-Markers$_{test}$)×100/Markers$_{ref}$ Values for Markers$_{ref}$ and Markers$_{test}$ are defined as follows:
Markers$_{ref}$=Total ABS/Squalene Markers (nmoles/L) of the fabrics washed with the formulation without oligoamine (e.g., the reference or control formulation)
Markers$_{test}$=Total ABS/Squalene Markers (nmoles/L) of the fabrics washed with the formulation with the tested oligoamine As the measured oxidation products are typically considered malodorous, it is believed that the greater the % reduction of oxidation products provided by a composition, the less malodorous the treated fabrics are likely to be. Therefore, greater values of % Malodor Reduction Oxidation Products are typically preferred. The compositions and processes of the present disclosure may provide a % Malodor Reduction Oxidation Products value of at least about 10%, or at least about 20%, or at least about 30%, or at least about 40%, or at least about 50%, or at least about 60%, or at least about 70%, or at least about 80%.

Whiteness Loss Test Method Test

The following procedures are followed to test for whiteness losses (e.g., ΔWI).

A. Preparation of Whiteness Test Fabrics

De-sized Cotton, Polycotton and Polyester whiteness test fabrics can be ordered from WFK. (WFK Testgewebe GmbH, Christenfeld 10, D-41379 Brüggen, Germany). Four of each fabric type (12 fabrics total) are prepared for the whiteness test by washing them four times in 48 grams (750 ppm) of Tide Free and Clear and 25 grams (390 ppm) Downy Free rinse in a Kenmore Top Loader set to Normal wash cycle, 77 F wash, 60 F rinse, 7 grains per gallon. An initial whiteness reference measurement is made using Konica Minolta spectrophotometer and reported as Initial Whiteness Index CIE. The Whiteness Index CIE value is a common index of whiteness and refers to measurements made under D65 illumination, the standard representation of outdoor daylight. For a perfect reflecting, non-fluorescent white material, the CIE Whiteness would be 100. In technical terms, whiteness is a single number index referencing the relative degree of whiteness of near-white materials under specific lighting conditions. The index has been devised such that most people will agree that the higher the whiteness index, the whiter the material.

B. Whiteness Test

Fabrics are placed in a 7.57 liter custom washing tub under the conditions summarized in Table 3 below. Fabrics are washed with 5.65 grams (746 ppm) of detergent (liquid TIDE®) in the wash cycle together with background soil, followed by 3 grams (396 ppm) liquid fabric softener (DOWNY® Free) in the rinse cycle. Once the rinse cycle is complete, all the fabrics are removed and placed in a tumble dryer. This is repeated for 10 wash, rinse and dry cycles. After 10 cycles, fabrics are measured for whiteness loss using a Konica Minolta spectrophotomer and the measurement is reported as Final Whiteness Index. An average delta WI (i.e., ΔWI), representing the difference in the whiteness index measurements between the initial and treated, is calculated for each fabric tested, and represented by the following calculation: ΔWI=Initial Whiteness Index after preparation—Treated Whiteness Index after 10-20 cycles. Typically, ΔWI is a negative value as the whiteness tends to decrease after washing with background soil. The whiteness index is reported in the table as ΔΔWI=ΔWI test with oligoamine–ΔWI REF (nil oligoamine). ΔΔW is a negative value if the whiteness tends to decrease after washing with a test liquid detergent composition containing a oligoamine compared to a reference liquid detergent composition that does not contain an oligoamine. Numbers close to zero would represent an oligoamine which has little impact on fabric yellowing.

TABLE C

| Wash, Rinse and Drying Conditions | |
|---|---|
| Setting | |
| Agitation (strokes per min) | 80 spm (Normal) |
| Wash Temperature | 60 F. |
| Water Hardness | 7 gpg |
| Rinse Temperature | 60 F. |
| Wash Cycle Time | 45 second liquid pre-dissolve, 18 min cycle |
| Rinse Cycle Time | 2 min cycle |
| Tub Volume | 7.57 liters |
| Drying Time | 35-40 min High heat setting (or until dry) |
| Background Soil | 1 Artificial Body Soil Terry Artificial body soil terry is commercially available by Accurate Product Development; 2028 Bohlke Blvd, Fairfield, OH 45014. 1 SBL2004 sheets from WFK Testgewebe GmbH Optionally, dingy fabrics as supplied by consumers |
| Internal fabric replicates | 4 Cotton (CW 120), 4 Polycotton (PC 50/50), 4 Polyester (PW 19) |

EXAMPLES

The examples provided below are intended to be illustrative in nature and are not intended to be limiting.

Example 1. Exemplary Formulations (Heavy Duty Liquid Laundry Detergents)

The following heavy duty liquid laundry detergent compositions may be prepared by traditional means known to those of ordinary skill in the art by mixing the listed ingredients Table 1. Composition 1A is a conventional premium laundry detergent that contains no linear oligoamines of the present disclosure. Composition 1B is a comparative example that includes EDDS chelant.

TABLE 1

| Raw Material | 1A Active Wt % (comp) | 1B Active Wt % (comp) | 1C Active Wt % | 1D Active Wt % | 1E Active Wt % |
|---|---|---|---|---|---|
| C12-15 alkyl ethoxy (1.8) sulfate | 11.7 | 11.7 | 11.7 | 11.7 | 11.7 |
| Alkyl benzene sulfonate[1] | 7.2 | 7.2 | 7.2 | 7.2 | 7.2 |
| C12-14 Amine Oxide | 0.7 | 0.7 | 0.7 | 0.7 | 0.7 |
| C12-14 EO9[2] | 5 | 5 | 5 | 5 | 5 |
| Citric Acid | 2.1 | 2.1 | 2.1 | 2.1 | 2.1 |
| C12-18 Fatty Acid | 0.9 | 0.9 | 0.9 | 0.9 | 0.9 |
| Sodium hydroxide | 0.2 | 0.2 | 0.2 | 0.2 | 0.2 |
| Chelant[3] | 0.47 | 0.47 | 0.47 | 0.47 | 0.47 |
| Ethylenediaminedisuccinic acid (EDDS chelant) | — | 0.5 | — | — | — |
| Oligoamine 1[9] | — | — | 0.1 | — | — |
| Oligoamine 2[10] | — | — | — | 0.1 | — |
| Oligoamine 3[11] | — | — | — | — | 0.1 |
| Monoethanolamine (MEA) | 2.9 | 2.9 | 2.9 | 2.9 | 2.9 |
| Diethylene glycol (DEG) | 2.4 | 2.4 | 2.4 | 2.4 | 2.4 |
| 1,2-Propanediol | 2.1 | 2.1 | 2.1 | 2.1 | 2.1 |
| Borate | 1 | 1 | 1 | 1 | 1 |
| Ethanol | 1.5 | 1.5 | 1.5 | 1.5 | 1.5 |
| Sorbitol | 0.06 | 0.06 | 0.06 | 0.06 | 0.06 |
| Sodium Cumene Sulfonate | 0.15 | 0.15 | 0.15 | 0.15 | 0.15 |
| Ethoxylated Polyethyleneimine [4] | 1.5 | 1.5 | 1.5 | 1.5 | 1.5 |
| Amphiphilic alkoxylated grease cleaning polymer[5] | 1.3 | 1.3 | 1.3 | 1.3 | 1.3 |
| Calcium formate | 0.1 | 0.1 | 0.1 | 0.1 | 0.1 |
| Sodium Chloride | 0.03 | 0.03 | 0.03 | 0.03 | 0.03 |
| Protease[6] | 0.068 | 0.068 | 0.068 | 0.068 | 0.068 |
| Mannanase[7] | 0.002 | 0.002 | 0.002 | 0.002 | 0.002 |
| Amalyse[7] | 0.007 | 0.007 | 0.007 | 0.007 | 0.007 |
| Fluorescent Whitening Agents[8] | 0.3 | 0.3 | 0.3 | 0.3 | 0.3 |
| V200 Whiteness Dye | 0.025 | 0.025 | 0.025 | 0.025 | 0.025 |
| Perfume | 0.6 | 0.6 | 0.6 | 0.6 | 0.6 |
| Hydrogenated Castor Oil | 0.1 | 0.1 | 0.1 | 0.1 | 0.1 |
| Phenoxyethanol | 0.001 | 0.001 | 0.001 | 0.001 | 0.001 |
| Benzisothiazolinone | 0.001 | 0.001 | 0.001 | 0.001 | 0.001 |
| Aesthetic dye | 0.01 | 0.01 | 0.01 | 0.01 | 0.01 |
| DC1520 Silicone Suds suppressor | 0.003 | 0.003 | 0.003 | 0.003 | 0.003 |
| AF8017 Silicone Suds suppressor | 0.2 | 0.2 | 0.2 | 0.2 | 0.2 |
| Water/Misc. | Balance | Balance | Balance | Balance | Balance |

[1] Linear alkylbenzenesulfonate having an average aliphatic carbon chain length C11-C12 supplied by Stepan, Northfield, Illinois, USA

[2] AE9 is C12-14 alcohol ethoxylate, with an average degree of ethoxylation of 9, supplied by Huntsman, Salt Lake City, Utah, USA

[3] Diethylenetetraamine pentaacetic acid (DTPA) supplied by Dow Chemical, Midland, Michigan, USA; Hydroxyethane diphosphonate (HEDP) supplied by Solutia, St Louis, Missouri, USA Bagsvaerd, Denmark, may also be used

[4] Polyethyleneimine (MW = 600) with 20 ethoxylate groups per —NH.

[5] Amphiphilic alkoxylated grease cleaning polymer is a polyethyleneimine (MW = 600) with 24 ethoxylate groups per —NH and 16 propoxylate groups per —NH.

[6] Proteases may be supplied by Genencor International, Palo Alto, California, USA (e.g. Purafect Prime ®) or by Novozymes, Bagsvaerd, Denmark (e.g. Liquanase ®, Coronase ®).

[7] Natalase ®, Mannaway ® are all products of Novozymes, Bagsvaerd, Denmark.

[8] Suitable Fluorescent Whitening Agents are for example, Tinopal ® AMS, Tinopal ® CBS-X

[9] Diethylenetriamine (DETA)

[10] N,N'-Bis (3-aminopropyl)ethylenediamine

[11] Tetraethylenepentamine (TEPA)

Example 2. Malodor Control of Oligoamines Vs. Known Chelant

To show the malodor control effects of oligoamines of the present disclosure, various liquid detergent compositions are prepared according to Example 1A, Table 1, above. Some have one or more conventional chelating agents; some include linear oligoamines according to the present disclosure.

Example 2A is a premium-type laundry detergent that contains conventional chelant (diethylenetetraamine pentaacetic acid (DTPA)). Additional amines are added for Examples 2B, 2C, 2D, and 2E. Examples 2B is contains an additional amino chelating agent, ethylenediaminedisuccinic acid (EDDS). Examples 2C, 2D and 2E contain oligoamines of the present disclosure, as detailed below in Table 2. The compositions are tested for % Reduction Oxidation Products according to the test method provided above. Results are shown in Table 2.

TABLE 2

| Example | Liquid Composition | Additional amine | Mole Ratio Anionic Surfactant to Protonable Amine | % Reduction Oxidation Products vs. REF |
|---|---|---|---|---|
| 2A (REF) | 1A | None | — | (REF) |
| 2B | 1B | EDDS | — | 6 |
| 2C | 1C | DETA | 26 | >70 |
| 2D | 1D | N,N'-Bis (3-aminopropyl) ethylenediamine[1] | 29 | >70 |
| 2E | 1E | TEPA | 24 | >70 |

[1]N,N'-Bis (3-aminopropyl) ethylenediamine has the following structure:

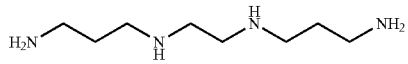

The results in Table 2 show the malodor control benefits of linear oligoamines of Examples 2C, 2D, and 2E compared to the nil-additional-amine composition of 2A. Examples 2C, 2D, and 2E also show improved malodor control compared to Example 2B, indicating that the oligoamines perform better than EDDS, a different amine-containing chelant.

Example 3. Malodor Control of Linear Oligoamines Vs. Other Amines (1)

To show the malodor control benefits of oligoamines of the present disclosure compared to other amines, various additional amines are formulated into liquid detergent composition A (see Example 1, Table 1, above) as provided in Table 3. Fabrics are treated with the compositions in a North-American-style top loader machine. The compositions are tested for % Reduction Oxidation Products according to the test method provided above. Results are shown in Table 3.

TABLE 3

| Example | Additional Amine | % Reduction Oxidation Products vs. REF F |
|---|---|---|
| 3A (REF) | — | (REF) |
| 3B | 0.2% DETA[1] | 35% |
| 3C | 0.2% Methylated DETA[2] | 54% |
| 3D (comp) | 0.2% Dytec DHC-99[3] | 6% |
| 3E (comp) | 0.2% Jeffamine EDR148[4] | −3% |
| 3F (comp) | 0.2% Dytec EP[5] | 0% |

[1]DETA is Diethylenetriamine, commercially supplied by Aldrich:

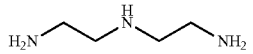

[2]Methylated DETA is N1-(2-aminoethyl)-N1-methylethane-1,2-diamine:

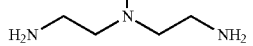

[3]Dytec DHC 99 is 1,2-Diaminocyclohexane, commercially supplied by Aldrich:

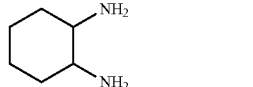

[4]Jeffamine ERD 148 is 2,2'-(ethane-1,2-diylbis(oxy))bis(ethan-1-amine), commercially supplied by Huntsman:

[5]Dytec EP is 1,3-Pentanediamine commercially supplied by Aldrich:

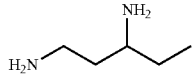

As shown in Table 3, Examples 3B and 3C, which include linear oligoamines according to the present disclosure show improved malodor control benefits compared to the control composition (Example 3A). Comparative Examples 3D, 3E, and 3F, on the other hand, do not show comparable malodor control benefits according to the data of Table 3.

Example 4. Malodor Control of Oligoamines Vs. Other Amines (2)

To show the malodor control benefits of oligoamines of the present disclosure compared to other amines, various additional amines are formulated into liquid detergent composition A (see Example 1, Table 1, above) as provided in Table 4. Fabrics are treated with the compositions in a North-American-style top loader machine. The compositions are tested for % Reduction Oxidation Products according to the test method provided above. Results are shown in Table 4.

TABLE 4

| Example | Additional amine | % Reduction Oxidation Products vs. REF |
|---|---|---|
| 4A (REF) | — | (REF) |
| 4B | 0.1% DETA | 35 |
| 4C | 0.1% N1-(3-aminopropyl)-N1-methylpropane-1,3-diamine[1] | 20 |
| 4D (comp) | 0.1% Dytec DHC99 | 0 |
| 4E (comp) | 0.1% Jeffamine ERD148 | 0 |
| 4F (comp) | 0.1% Dytec EP | 0 |

[1]N1-(3-aminopropyl)-N1-methylpropane-1,3-diamine has the following structure:

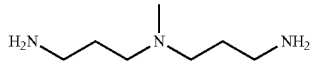

As shown in Table 4, Examples 4B and 4C, which include oligoamines according to the present disclosure show improved malodor control benefits compared to the control composition (Example 4A). Comparative Examples 4D, 4E, and 4F, on the other hand, do not show comparable malodor control benefits according to the data of Table 4.

Example 5. Malodor Control of DETA

To show the malodor control benefits of diethylenetriamine (DETA), various amounts of DETA is formulated into liquid detergent composition 1A (see Table 1, above) according to the amounts (provided as weight %, by weight of the composition) provided in Table 5. Test fabrics were treated in a front-loader machine; the amount of DETA present in the treatment liquor is provided as parts per million (ppm). Table 5 also provides the mole ratio of anionic surfactant to protonable amines present in the oligoamine. The compositions are tested for % Reduction Oxidation Products according to the test method provided above.

TABLE 5

| Example | Amount of DETA present in composition (wt %) | Amount of DETA present in treatment liquor (ppm) | Mole Ratio: Anionic Surfactant to Protonatable Amine | Total ABS/ Squalene Markers (nmoles/L) | % Reduction Oxidation Products vs. REF |
|---|---|---|---|---|---|
| 5A (REF) | 0.00 wt % | 0 ppm | — | 102.5 | (REF) |
| 5B | 0.05 wt % | 1.3 ppm | 52 | 47 | 54 |
| 5C | 0.09 wt % | 2.4 ppm | 28 | 21 | 80 |
| 5D | 0.1 wt % | 2.5 ppm | 26 | 20 | 80 |
| 5E | 0.15 wt % | 3.8 ppm | 17 | 15 | 85 |

The results shown in Table 5 illustrate the malodor prevention on textiles washed in liquid compositions containing linear oligoamine of the present disclosure in a composition according to Example 1A compared to similar detergent without linear oligoamine, even when the amine is present in the composition at levels at or below 0.1 wt %, and/or in the treatment liquor at levels below 4 ppm, or even below 3 ppm.

Example 6. Oligoamine and Antioxidant

To show the malodor control benefits of oligoamines of the present disclosure, including in combination with antioxidant, a liquid detergent composition according to Example 1A in Example 1, Table 1 above is provided. Various combinations of a linear oligoamine and antioxidant are added to the liquid detergent composition in the levels provided in Table 6. The antioxidant added to Examples 6D and 6E is a hindered phenol antioxidant (specifically, octadecyl 3-(3,5-di-tert-butyl-4-hydroxyphenyl)propionate, sold commercially as Tinogard TS (ex BASF)).

The compositions are tested for % Reduction Oxidation Products according to the test method provided above. Results are shown in Table 6.

TABLE 6

| Example | Additional amine (DETA) | Antioxidant (hindered phenol) | % Reduction Oxidation Products vs. REF |
|---|---|---|---|
| 6A (REF) | — | — | REF |
| 6B | 0.05 wt % | — | 44 |
| 6C | 0.1 wt % | — | >80 |
| 6D | — | 0.05 wt % | 0 |
| 6E | 0.05 wt % | 0.01 wt % | 74 |

As shown in Table 6, the presence of the DETA amine results in improved malodor control. The data in Table 6 further shows that the tested combination of an oligoamine according to the present disclosure and an antioxidant provides improved malodor control.

Notably, although the level of DETA is the same in Liquid Compositions 6B and 6E, Liquid Composition 6E (which further comprises antioxidant) provides almost twice the percentage of oxidation products removal. Further, the performance of Liquid Composition 6E is on par with the performance of Liquid Composition 6C, which comprises twice as much of the DETA amine.

Example 7. Effects of Alkylation

To show the effects that various degrees of alkylation of the presently described oligoamines can have on malodor reduction benefits, the following molecules are tested at the provided levels according to the test method provided above. The tests are run in a North American front-loading automatic washing machine.

The percentage reduction of oxidation products vs. the reference composition are provided for each compound below in Tables 7A and 7B.

TABLE 7A

| Example | Oligoamine (0.2 wt %) | Structure | % Reduction Oxidation Products vs. REF |
|---|---|---|---|
| 7A (REF) | Nil-Oligoamine (0%) | — | REF |
| 7B | 0.2% DETA | 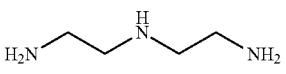 | 94 |
| 7C | 0.2% M3s-DETA | 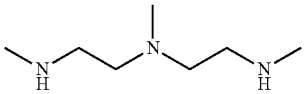 | 54 |

TABLE 7A-continued

| Example | Oligoamine (0.2 wt %) | Structure | % Reduction Oxidation Products vs. REF |
|---|---|---|---|
| 7D | 0.2% M5s-DETA | (structure) | 31 |

As shown by the structures above, Example 7B features terminal primary amines, Example 7C features terminal secondary amines, and Example 7D features terminal tertiary amines. As shown in Table 7A, Examples 7B-7D each provide malodor reduction benefits, with Example 7B providing the relatively greatest malodor reduction.

TABLE 7B

| Example | Oligoamine (0.1 wt %) | Structure | % Reduction Oxidation Products vs. REF |
|---|---|---|---|
| 7E (REF) | Nil-Oligoamine (0%) | — | REF |
| 7F | 0.1% DETA | (structure) | 91 |
| 7G | 0.1% M1s-DETA | (structure) | 85 |
| 7H | 0.1% M3s-DETA | (structure) | 26 |
| 7I | 0.1% M5s-DETA | (structure) | 0 |

As shown in Table 7B, Example 7F provides the relatively greatest malodor reduction.

Example 8. Oligoamine Vs. Whiteness

To show the effect that oligoamines (and % levels thereof) can have on whiteness, certain amines are added to North American liquid TIDE® (a commercially available heavy duty liquid laundry detergent) as provided in Table 8. Various fabrics (cotton, polycotton, and polyester) are treated under North American conditions for ten wash cycles with the compositions.

After ten cycles, whiteness losses are determined according to the Whiteness Loss Test Method, as provided above in the Test Methods section. Results are provided in Table 8. Negative numbers show whiteness losses, with numbers of greater magnitude indicating greater whiteness losses (e.g., −10 indicates more whiteness loss than −5). It is preferred that the whiteness losses are between 0 and −5, or between 0 and −4. Whiteness losses that are greater in magnitude indicate that the product may be less preferred for consumer use.

TABLE 8

| Trial | Amine (wt %) | Cotton ΔΔWI vs REF | Polycotton ΔΔWI vs REF | Polyester ΔΔWI vs REF |
|---|---|---|---|---|
| 8A (REF: TIDE ®) | — | 0.0 | 0.0 | 0.0 |
| 8B | 0.094% DETA | −4.5 | −4.7 | −3.9 |
| 8C | 0.04% N,N'-Bis (3-aminopropyl) ethylenediamine | −3.0 | −5.7 | −3.7 |
| 8D | 1.2% DETA | −16.5 | −19.5 | −19.2 |

As shown in Table 8, the presence of amines may result in whiteness losses upon multiple treatments. However, the whiteness losses provided by amine levels of, e.g., less than 0.1 wt % (see Trials 8B and 8C) are relatively acceptable to a manufacturer. By way of comparison, Trial 8D, which includes DETA levels of above 1%, shows whiteness losses that are believed to be less preferred. It is believed that alkylated oligoamines may further improve whiteness losses and/or allowing the oligoamines to be formulated at relatively higher levels while keeping whiteness losses within an acceptable range.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A treatment composition comprising:
   from about 0.01% to about 0.2%, by weight of the treatment composition, of an oligoamine and/or a salt thereof,
   wherein the oligoamine is diethylenetriamine (DETA);
   from about 5% to about 40%, by weight of the treatment composition, of a surfactant system,
   wherein the surfactant system comprises anionic surfactant,
   wherein the anionic surfactant comprises linear alkyl benzene sulfonate (LAS), alkyl ethoxylated sulfate (AES), alkyl sulfates (AS), or mixtures thereof,
   wherein the surfactant system further comprises nonionic surfactant,
   wherein the nonionic surfactant comprises alkoxylated fatty alcohols having from about 12 to about 16 carbon atoms, and an average of from about 3 to about 9 ethoxy groups;
   an additional chelating agent selected from the group consisting of diethylenetriaminepentaacetic acid, hydroxy ethanediphosphonic acid, ethylenediamine disuccinate, diethylene triamine penta(methylenephosphonic acid), ethylene diamine tetra(methylenephosphonic acid), 1,2-dihydroxybenzene-3,5-disulfonic acid, 2-pyridinol-N-oxide, methylglycinediacetic acid, glutamic-N,N-diacetic acid, any suitable derivative thereof; salts thereof; and mixtures thereof; and
   an additional treatment adjunct;
   wherein the treatment composition is a liquid laundry detergent.

2. A treatment composition according to claim 1, wherein the additional treatment adjunct is selected from a fabric conditioning active (FCA), antioxidant, hueing agent, optical brightener, enzymes, fatty acids and/or salts thereof, encapsulated benefit agents, soil release polymers, builders, dye transfer inhibiting agents, dispersants, enzyme stabilizers, catalytic materials, bleaching agents, bleach catalysts, bleach activators, polymeric dispersing agents, soil removal/anti-redeposition agents, polymeric grease cleaning agents, amphiphilic copolymers, suds suppressors, aesthetic dyes, perfume, structure elasticizing agents, fabric softeners, carriers, fillers, hydrotropes, solvents, anti-microbial agents and/or preservatives, pH adjusting agents, processing aids, fillers, rheology modifiers, structurants, opacifiers, pearlescent agents, pigments, anti-corrosion agents, anti-tarnishing agents, antifoams, chlorine scavengers, and mixtures thereof.

3. A treatment composition according to claim 1, wherein the anionic surfactant is pre-neutralized with an alkali metal, an alkali earth metal, an amine, or mixtures thereof.

4. A treatment composition according to claim 1 wherein the mole ratio of anionic surfactant to protonatable amines in the oligoamine is less than about 15:1.

5. A treatment composition according to claim 1, wherein the additional treatment adjunct comprises an antioxidant.

6. A treatment composition according to claim 1, wherein the additional treatment adjunct comprises a whitening or brightening agent selected from the group consisting of a hueing agent, an optical brightener, and mixtures thereof.

7. A treatment composition according to claim 1, wherein the oligoamine and the additional chelant are present in the treatment composition at a combined level of from about 0.1% to about 10%, by weight of the treatment composition.

8. A treatment composition according to claim 1, wherein the weight ratio of the oligoamine to the additional chelant is from about 10:1 to about 1:50.

9. A treatment composition according to claim 1, wherein the additional treatment adjunct comprises an enzyme selected from the group consisting of protease, amylase, lipase, cellulase, phosphodiesterase, pectate lyase, and mixtures thereof.

10. A treatment composition according to claim 1, wherein the treatment composition is in a form selected from a liquid composition, a granular composition, a single-compartment pouch, a multi-compartment pouch, a dissolvable sheet, a pastille or bead, a fibrous article, a tablet, a bar, a flake, a dryer sheet, and mixtures thereof.

11. A process of treating a surface, the process comprising the steps of:
    providing a surface, and
    contacting the surface with a composition according to claim 1, optionally in the presence of water.

12. A treatment composition according to claim 5, wherein the antioxidant comprises a hindered phenol antioxidant.

13. A treatment composition according to claim 12, wherein the hindered phenol antioxidant is selected from the group consisting of: 2,6-bis(1,1-dimethylethyl)-4-methylphenol; 3,5-bis(1,1-dimethylethyl)-4-hydroxy-benzenepropanoic acid, methyl ester; 3,5-bis(1,1-dimethylethyl)-4-hydroxybenzenepropanoic acid, octadecyl ester; and mixtures thereof.

14. A treatment composition according to claim 1, wherein the additional chelating agent is diethylenetriaminepentaacetic acid.

* * * * *